US011154587B2

(12) United States Patent
Tamarit et al.

(10) Patent No.: US 11,154,587 B2
(45) Date of Patent: Oct. 26, 2021

(54) USE OF PEPTIDES TO STIMULATE THE IMMUNE SYSTEM

(71) Applicant: DIACCURATE, Paris (FR)

(72) Inventors: Blanche Tamarit, Paris (FR); Jacques Theze, Paris (FR)

(73) Assignee: DIACCURATE, Paris (FR)

( * ) Notice: Subject to any disclaimer, the term of this patent is extended or adjusted under 35 U.S.C. 154(b) by 88 days.

(21) Appl. No.: 15/766,458

(22) PCT Filed: Oct. 7, 2016

(86) PCT No.: PCT/EP2016/073960
§ 371 (c)(1),
(2) Date: Apr. 6, 2018

(87) PCT Pub. No.: WO2017/060405
PCT Pub. Date: Apr. 13, 2017

(65) Prior Publication Data
US 2018/0296632 A1 Oct. 18, 2018

(30) Foreign Application Priority Data
Oct. 9, 2015 (EP) .................................... 15306597

(51) Int. Cl.
A61K 38/00 (2006.01)
A61K 38/02 (2006.01)
A61K 38/12 (2006.01)
C07K 7/06 (2006.01)
A61K 38/13 (2006.01)
A61K 45/06 (2006.01)
C07K 7/64 (2006.01)

(52) U.S. Cl.
CPC ............ A61K 38/12 (2013.01); A61K 38/005 (2013.01); A61K 38/13 (2013.01); A61K 45/06 (2013.01); C07K 7/06 (2013.01); C07K 7/64 (2013.01)

(58) Field of Classification Search
None
See application file for complete search history.

(56) References Cited

U.S. PATENT DOCUMENTS

| 10,894,035 | B2 | 1/2021 | Theze et al. |
| 2016/0311926 | A1 | 10/2016 | Theze |
| 2018/0344694 | A1 | 12/2018 | Theze et al. |
| 2020/0397855 | A1 | 12/2020 | Pothlichet et al. |
| 2020/0399392 | A1 | 12/2020 | Pothlichet et al. |

FOREIGN PATENT DOCUMENTS

| WO | WO 99/41278 | 8/1999 |
| WO | WO 2015/097140 | 7/2015 |
| WO | WO 2017/037041 | 3/2017 |

OTHER PUBLICATIONS

Das et al., "Role of lipids in sepsis," Crit Care & Shock 7: 87-92 (2004) (Year: 2004).*
Merck Manual (https://www.merckmanuals.com/professional/infectious-diseases/viruses/overview-of-viruses accessed Feb. 19, 2019) (Year: 2019).*
Merck Manual (https://www.merckmanuals.com/home/skin-disorders/fungal-skin-infections/overview-of-fungal-skin-infections accessed Feb. 19, 2019) (Year: 2019).*
Merck Manual—fungal infections overview (https://www.merckmanuals.com/professional/infectious-diseases/fungi/overview-of-fungal-infections accessed Oct. 21, 2020) (Year: 2020).*
Merck Manual (https://www.merckmanuals.com/professional/infectious-diseases/approach-to-parasitic-infections/approach-to-parasitic-infections?query=protozoa accessed Oct. 22, 2020 (Year: 2020).*
Weiner, "multiple sclerosis is an inflammatory T-cell mediated autoimmune disease," Arch. Neurol. 61:1613-1615 (2004) (Year: 2004).*
Ohashi, "T-cell signaling and autoimmunity: molecular mechanisms of disease," Nat. Rev. 2:427-438 (2002) (Year: 2002).*
Hata, "Distinct contribution of IL-6, TNF-α, IL-1, and IL-10 to T cell-mediated spontaneous autoimmune arthritis in mice," J. Clin. Invest. 114:582-588 (2004) (Year: 2004).*
Merck Manual (https://www.merckmanuals.com/professional/immunology-allergic-disorders/immunodeficiency-disorders/overview-of-immunodeficiency-disorders?query=immunodeficiency accessed Oct. 22, 2020) (Year: 2020).*
Murakami et al., "Secretory Phospholipase A2" Biol. Pharm. Bull. 27:1158-1164 (2004) (Year: 2004).*
Dimitrov, "Virus Entry:Molecular Mechanismsand Biomedical Applications," Nature reviews 2:109-122 (2004) (Year: 2004).*
Douek, "Disrupting T-cell homeostasis: how HIV-1 infection causes disease," AIDS reviews 5:172-177 (2003) (Year: 2003).*
Chandra, V. et al. "Crystal Structure of a Complex Formed between a Snake Venom Phospholipase $A_2$ and a Potent Peptide Inhibitor Phe-Leu-Ser-Tyr-Lys at 1.8 A Resolution" The Journal of Biological Chemistry, Oct. 25, 2002, pp. 41079-41085, vol. 277, No. 43.
Church, W. B. et al. "A Novel Approach to the Design of Inhibitors of Human Secreted Phospholipase $A_2$ Based on Native Peptide Inhibition" The Journal of Biological Chemistry, Aug. 31, 2001, pp. 33156-33164, vol. 276, No. 35.
Tseng, A. et al. "Native Peptide Inhibition" The Journal of Biological Chemistry, Sep. 27, 1996, pp. 23992-23998, vol. 271, No. 39.
Written Opinion in International Application No. PCT/EP2016/073960, dated Dec. 13, 2016, pp. 1-7.
Claims as filed for U.S. Appl. No. 16/976,485, 2020 pp. 1-4.
Claims as filed for U.S. Appl. No. 16/976,486, 2020 pp. 1-3.

* cited by examiner

Primary Examiner — Julie Ha
Assistant Examiner — Kristina M Hellman
(74) Attorney, Agent, or Firm — Saliwanchik, Lloyd & Eisenschenk

(57) ABSTRACT

Methods for treating immunodeficiencies are provided using peptide-based compounds.

12 Claims, 2 Drawing Sheets
Specification includes a Sequence Listing.

USE OF PEPTIDES TO STIMULATE THE IMMUNE SYSTEM

CROSS-REFERENCE TO RELATED APPLICATION

This application is the U.S. national stage application of International Patent Application No. PCT/EP2016/073960, filed Oct. 7, 2016.

The Sequence Listing for this application is labeled "Seq-List.txt" which was created on Mar. 30, 2018 and is 3 KB. The entire content of the sequence listing is incorporated herein by reference in its entirety.

FIELD OF THE INVENTION

The present invention relates to compositions and methods to induce or stimulate an immune response in a subject using particular peptide-based compounds. The invention is particularly effective for stimulating CD4 T cells and may be used to treat HIV infected patients.

INTRODUCTION

CD4 T lymphocytes play a pre-eminent role in controlling the immune system (both cellular and humoral responses) and are critical in various disease conditions such as cancer or infectious diseases.

During the immunological disease associated with HIV pathogenesis, less than 0.5% of all CD4 T cells are actually infected (as measured in the peripheral blood), but the great majority of CD4 T cells shows major regulatory dysfunction. Uninfected CD4 T lymphocytes progressively lose their function, become anergic, and their numbers decrease resulting in CD4 lymphopenia. Anergy and lymphopenia are the hallmarks of the immunodeficiency characterizing HIV-infected patients. The mechanisms behind these phenomena have never been fully elucidated (1). Immune activation and inflammation also play a critical role in HIV pathogenesis (2, 3).

The inventors have previously reported the identification, isolation and characterization, from human plasma, of the protein responsible for this aberrant state of CD4 T cell activation, designated sPLA2G1B (WO2015/097140).

The present invention relates to the use of particular peptides that are able to inhibit sPLA2G1B and to stimulate the immune system in a subject in need thereof. More particularly, the inventors have selected a particular group of peptide-based compounds that exhibit potent sPLA2G1B inhibitory effect. The inventors have demonstrated that these compounds are able to completely neutralize the capacity of sera from viremic HIV-infected patients to induce abnormal and pathogenic responses in the CD4 lymphocytes purified from healthy donors, and thus to restore CD4 T cell function in HIV infected subjects.

SUMMARY OF THE INVENTION

An object of the invention relates to a method for stimulating or inducing an immune response in a subject, comprising exposing the subject to a compound of formula A, or a salt, ester, hydrate, racemate, enantiomer, prodrug or metabolite thereof.

A further object of the invention relates to a method of treatment of an immunodeficiency disorder in a subject, comprising exposing the subject to a compound of formula A, or a salt, esther, hydrate, racemate, enantiomer, prodrug or metabolite thereof.

Another object of the invention relates to the use of a compound of formula A, or a salt, ester, hydrate, racemate, enantiomer, prodrug or metabolite thereof, for the manufacture of a medicament for inducing or stimulating an immune response or for treating an immunodeficiency disorder in a subject.

Another object of the invention relates to a compound of formula A, or a salt, ester, hydrate, racemate, enantiomer, prodrug or metabolite thereof, for use in a method of inducing or stimulating an immune response or of treating an immunodeficiency disorder in a subject.

The invention is particularly suited to treat immunodeficient subjects or subject in need of stimulated immunity (e.g., subjects having an infectious disease or a cancer). In this regard, a particular object of the invention resides in a method of treating an infectious disease in a subject, comprising administering to the subject a compound of formula A or a salt, ester, hydrate, racemate, enantiomer, prodrug or metabolite thereof.

A more particular embodiment of the invention relates to a method of treating AIDS in a HIV-infected subject, comprising administering to the subject a compound of formula A or a salt, ester, hydrate, racemate, enantiomer, prodrug or metabolite thereof.

In another aspect, the invention relates to a pharmaceutical composition comprising (i) a compound of formula A, or a salt, ether, hydrate, racemate, enantiomer, prodrug or metabolite thereof and (ii) a further antiviral or anticancer agent.

The invention may be used in any mammal, including humans and non-human animals such as, without limitation, domesticated animals (e.g., cows, sheep, cats, dogs, and horses), non-human primates (such as monkeys), rabbits, and rodents (e.g., mice and rats). It is particularly suited for use in human subjects. It may be used to increase the immune response in any mammal, and it is particularly adapted to induce potent CD4-T cell activity in immunodepressed subjects.

DETAILED DESCRIPTION OF THE INVENTION

Figure 1:
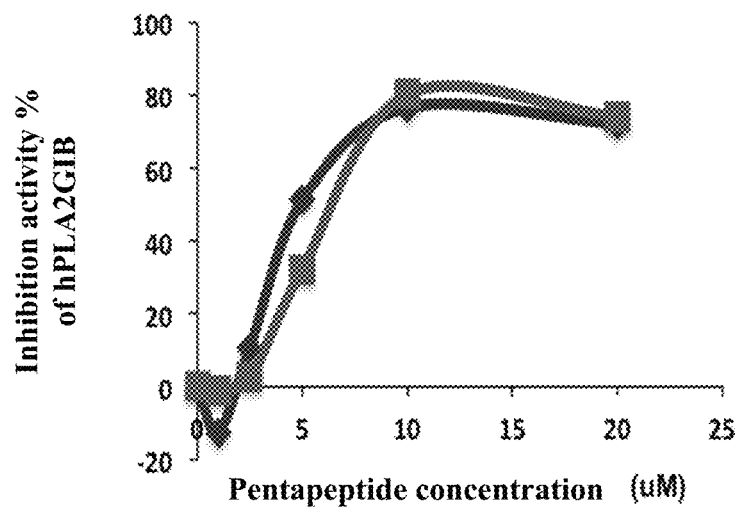
FIG. 1: Peptide I inhibits sPLA2G1B: Recombinant PLA2G1B (75 nanoM) was first exposed 30 mn to indicated concentrations of Peptide I. The mixture was then applied in the bioassay described in Materials and Methods. % inhibition of IL-7-induced nuclear translocation of phospho STAT5 was measured by STED microscopy. The results of two experiments are shown.

The present invention relates to compositions and methods for modulating the immune system in a subject in need thereof. The invention more particularly provides compositions and methods for stimulating the immune response or system, particularly in immunodepressed or immunodefective subjects.

The present invention discloses the remarkable capacity of particular peptides to completely neutralize PLA2G1B-mediated abnormal and pathogenic CD4 T lymphocytes. Remarkably, the effect of these compounds was found to be even more potent on PLA2GIB present in the plasma of patients than on the recombinant enzyme contained in serum free buffer. Such compounds thus represent novel and potent agents for stimulating the immune system in human subjects and, more particularly, for treating HIV-infected patients. Administered early during the infection process, they can prevent evolution towards an immune disease and prevent appearance of the immune deficiency. Given later, for instance in conjunction with Highly Active Anti-Retroviral Therapy (HAART), they facilitate the recovery of a functional immune system leading to a control of HIV infection by the immune system.

An object of the invention thus relates to a method for stimulating or inducing an immune response in a subject, comprising exposing the subject to a peptide of formula A, or a salt, ester, hydrate, racemate, enantiomer, prodrug or metabolite thereof.

A further object of the invention relates to a method of treatment of an immunodeficiency disorder in a subject, comprising exposing the subject to a peptide of formula A, or a salt, esther, hydrate, racemate, enantiomer, prodrug or metabolite thereof.

Another object of the invention relates to the use of a peptide of formula A, or a salt, ester, hydrate, racemate, enantiomer, prodrug or metabolite thereof, for the manufacture of a medicament for inducing or stimulating an immune response or for treating an immunodeficiency disorder in a subject.

The invention also relates to the use of peptides of formula A for stimulating or restoring CD4 T cells in a subject.

Peptides of Formula A

Peptides of formula A designate peptides comprising or consisting of the sequence AA1-Leu-AA3-AA4-AA5, wherein:

AA1 designates Phe, Leu, norleucine, tryptophan, 2-naphthylalanine (2NapA), or 1-naphthylalanine (1NapA);

AA3 designates Ser, Thr or Cys;

AA4 designates Tyr, 2-naphthylalanine (2NapA), 1-naphthylalanine (1NapA), diphenylalanine, 7-hydroxyltetrahydroisoquinoline (7HTiq), or tetrahydroisoquinoline (Tiq); and AA5 designates Lys, Arg, or citrulline.

Peptides of formula A have been described by Church et al., JBC 276(35) (2001) 33156 as inhibitors of human type IIA secreted phospholipase $A_2$ ($sPLA_2$-(GIIA). These peptides, however, were reported as rather selective for GIIA with no effect on e.g., porcine $sPLA_2$-GIB. Surprisingly, the inventors have discovered that peptides of formula A are potent inhibitors of sPLA2-GIB and exhibit a stimulatory effect on the immune system, particularly CD4 T lymphocytes. More particularly, the inventors have discovered that these peptides are able to completely neutralize sPLA2GIB-mediated CD4 anergy in HIV infected subjects, which was totally unknown.

Preferred peptides for use in the invention are peptides comprising the sequence AA1-Leu-Ser-AA4-AA5, or a pharmaceutically acceptable salt, hydrate, or prodrug thereof, wherein:

AA1 designates Phe, Leu, norleucine, tryptophan, 2-naphthylalanine (2NapA), or 1-naphthylalanine (1NapA), more preferably Phe or 2-naphthylalanine (2NapA);

AA4 designates Tyr, 2-naphthylalanine (2NapA), 1-naphthylalanine (1NapA), diphenylalanine, 7-hydroxyltetrahydroisoquinoline (7HTiq) or Tiq, more preferably Tyr or 2NapA; and AA5 designates Lys, Arg, or citrulline, preferably Lys or Arg.

In the peptides of the invention, the amino acids may be in D or L conformation. Also, peptides of the invention contain the above primary amino acid sequence and may contain one more additional chemical groups or substituents to further improve their activity or properties. In a preferred embodiment, their primary amino acid backbone does not contain more than 5 residues, although side chains may be derivatized with chemical groups or further amino acids. Preferred peptides of the invention are pentapeptides.

Most preferred peptides for use in the invention have a sequence selected from FLSYK (SEQ ID NO: 1), FLSYR (SEQ ID NO: 2), (2NapA)LS(2NapA)R (SEQ ID NO: 3, peptide I), (2NapA)LSYR (SEQ ID NO: 4) and FLS (2NapA)R (SEQ ID NO: 5).

Furthermore, in a preferred embodiment, the peptides for use in the invention are cyclic. Cyclization can be obtained during peptide synthesis using conventional techniques, or through ionic and/or hydrogen bonding.

In this regard, specific and preferred examples of peptides for use in the present invention are cyclic peptides FLSYK, FLSYR and (2NapA)LS(2NapA)R (peptide I).

Alternative peptides of formula A are peptides of less than 10 amino acids in length, preferably less than 9 amino acids in length, more preferably of 7, 6 or 5 amino acids in length, comprising anyone of the following amino acid sequences, or a pharmaceutically acceptable salt, hydrate, variant or prodrug thereof:

(SEQ ID NO: 6)
GCGSY (SEQ ID NO: 7)
GCGSP (SEQ ID NO: 8)
THTYS (SEQ ID NO: 9)
KDYYR (SEQ ID NO: 10)
LEKYL (SEQ ID NO: 11)
VDHYD (SEQ ID NO: 12)
TQSYK (SEQ ID NO: 13)
TERYS (SEQ ID NO: 14)
HETAW

Variants of such peptides designate peptides comprising the above primary amino acid sequence and containing one more additional chemical groups or substituents, to further improve their activity or properties. In a preferred embodiment, their primary amino acid backbone does not contain more than 5 residues, although side chains may be derivatized with chemical groups or further amino acids. In the peptides of the invention, the amino acids may be in D or L conformation. In a further particular embodiment, the peptides are cyclic.

Peptides for use in the invention may be produced according to methods known per se in the art such as by chemical peptide synthesis. For instance, the peptides can be prepared by t-butyloxycarbonyl chemistry on a solid phase synthesizer and/or using Fmoc (N-(9-fluorenyl)methoxycarbonyl) solid phase chemistry. Peptides can be cyclized by amide bond formation using standard peptide synthesis. Also, the peptides may contain one or more peptidomimetic bonds in order for instance to improve their stability. Examples of such peptidomimetic bonds include for instance intercalation of a methylene ($-CH_2-$) or phosphate ($-PO_2-$) group, secondary amine ($-NH-$) or oxygen ($-O-$), alpha-azapeptides, alpha-alkylpeptides, N-alkylpeptides, phosphonamidates, depsipeptides, hydroxymethylenes, hydroxyethylenes, dihydroxyethylenes, hydroxyethylamines, retro-inverso peptides, esters, phosphinates, phosphinics, phosphonamides and the like. In addition, the peptides may be further modified by addition or substitution of side chain residues.

The term "salt" refers to any pharmaceutically acceptable inorganic or organic acid/basic addition salt of a compound of the present invention. Pharmaceutically acceptable acid salts according to the invention include, without limitation, salts of trifluoroacetic acid, acetic acid, nitric acid, tartric acid, hydrochloric acid, sulfuric acid, phosphoric acid, methane sulfonic acid, oxalic acid, maleic acid, succinic acid or citric acid. Pharmaceutically acceptable basic salts of the invention include, without limitation, sodium, potassium, calcium, magnesium, ammonium, or choline salts.

The term "prodrug" as used herein refers to any functional precursor of a compound of structure A which, when administered to a biological system, generates said compound as a result of e.g., spontaneous chemical, enzymatic, biological and/or metabolic reaction(s). Typical prodrugs have the structure Y-A wherein Y is a protective group and is cleaved from the prodrug in vivo to release compound A. Prodrugs are usually inactive or less active than the resulting drug and can be used, for example, to improve the physicochemical or pharmacokinetic properties of a compound.

The term "metabolite" designates a molecule which results from the in vivo modification or processing of a compound A after administration to an organism. Such modifications may occur through specialized enzymatic systems leading to molecules retaining a biological activity of the compound.

The term "enantiomer" refers to isolated optically pure enantiomers, as opposed to a mixture (at any relative ratio) of isomers. Compounds for use in the invention may thus be optically pure enantiomers or any mixtures (e.g., racemate) thereof.

The peptides may be stored in solution or frozen or lyophilized, according to conventional techniques.

Compositions

The compounds for use according to the invention may be formulated with any pharmaceutically acceptable excipient, vehicle or carrier. They may be in the form of ointment, gel, paste, liquid solutions, suspensions, tablets, gelatin capsules, capsules, suppository, powders, nasal drops, or aerosol, preferably in the form of an injectible solution or suspension. For injections, the compounds are generally packaged in the form of liquid suspensions, which may be injected via syringes or perfusions, for example. In this respect, the compounds are generally dissolved in saline, physiological, isotonic or buffered solutions, compatible with pharmaceutical use and known to the person skilled in the art. Thus, the compositions may contain one or more agents or excipients selected from dispersants, solubilizers, stabilizers, preservatives, etc. Agents or excipients that can be used in liquid and/or injectable formulations are notably methylcellulose, hydroxymethylcellulose, carboxymethylcellulose, polysorbate 80, mannitol, gelatin, lactose, vegetable oils, acacia, etc. The carrier can also be selected for example from methyl-beta-cyclodextrin, a polymer of acrylic acid (such as carbopol), a mixture of polyethylene glycol and polypropylene glycol, monoetrhanol amine and hydroxymethyl cellulose.

The compositions generally comprise an effective amount of a compound of formula A, e.g., an amount that is effective to inhibit GIBsPLA2. Generally, the compositions according to the invention comprise from about 0.01 μg to 100 mg of a compound of formula A, for example between 0.05 μg and 50 mg, preferably between 0.05 μg and 5 mg, for example between 1 μg and 1 mg. The dosages may be adjusted by the skilled person depending on the disease and subject.

The compositions of the invention can further comprise one or more additional active compounds, for simultaneous or sequential use. In particular, compounds A may be used in combination with further anti-viral agents such as anti-retroviral agents.

The invention also relates to a pharmaceutical composition comprising a compound of formula A as defined above, a further antiviral agent and, optionally, a pharmaceutically acceptable excipient. The compositions of the invention may be formulated into any suitable device or container such as syringe, ampoule, flask, bottle, pouch, etc.

The invention also relates to a kit comprising (i) a container comprising a compound of formula A as previously described, (ii) a container comprising a further antiviral agent, and optionally (iii) written instructions for using the kit.

Diseases

The compounds and compositions of the invention may be used to treat any disease related to an inappropriate (e.g., defective or improper) immune response, particularly to an inappropriate CD4 T cell activity, as well as any disease where an increased immunity may ameliorate the subject condition. These diseases are sometime referred to as "immune disorders" or "immunodeficiencies" in the present application. This includes particularly immunodefective situations caused by viral infection or pathogenic infection, or cancers.

As used herein, the term "treatment" or "treat" refers for instance to any clinical intervention in an attempt to alter the natural course of the individual being treated, and can be performed either for preventive or curative purpose. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, compositions and methods of the invention are used to delay development of a disease or disorder or to slow the progression of a disease or disorder.

Examples of diseases that can benefit from such treatment are all diseases with an immunodeficiency such as HIV-mediated immunodeficiency. In this regard, in a particular embodiment, the invention is directed to methods for treating an immunodeficiency or an associated disorder in a subject in need thereof, comprising administering a compound of formula A to said subject.

In another particular embodiment, the invention is directed to a compound of formula A for use for treating an immunodeficiency or an associated disorder in a subject in need thereof.

Immunodeficiencies and associated disorders designate any condition or pathology characterized by and/or caused by a reduced immune function or response in a subject. Immunodeficiencies may be caused by e.g., viral infection (e.g., HIV, hepatitis B, etc.), bacterial infection, cancer, or other pathological conditions. The term "immunodeficiency-associated disorder" therefore designates any disease caused by or associated with an immunodeficiency. The invention is particularly suitable for treating immunodeficiencies related to CD4-T cells, and associated diseases.

In a particular embodiment, the invention relates to methods of treating HIV infection in a subject by administering a compound of formula A to said subject. In some embodiments the subject is an early HIV patient and the methods results in increasing the probability that the patient is a HIV controller, i.e., will not develop an immunodeficiency or will have a moderate or delayed immunodeficiency. In some embodiments the subject is a patient with low immunoreconstitution after antiretroviral treatment and/or with severe idiopatic CD4 T lymphopenia (ICL). The invention also relates to a method for increasing CD4-T cell activity in a HIV-infected subject by administering a compound of formula A to said subject.

The invention may be used to treat subjects at an early stage of the infection, to prevent or reduce occurrence, extent, or duration of an immunodeficiency. Typically, they can be administered immediately upon detection of an infectious disease, and prior to appearance of clinical signs. Administered very early during infection by HIV, compounds of formula A can lead the patients toward a HIV controller status. The compounds of the invention may also be administered later in infected subjects, either alone or in combination with antiviral agent(s). In such regimen, they accelerate the recovery of CD4 T lymphocytes and the restoration of their functions. Accordingly, in a particular embodiment, the invention comprises simultaneously, separately or sequentially administering to subject having a viral infection (i) an antiviral agent and (ii) a compound of formula A. Such protocol is particularly suited for treating HIV infected subjects, wherein compound A is used in combination with antiretroviral therapy (e.g., HAART), allowing to reduce HAART or even to at least temporarily interrupt HAART treatment which is known for its severe detrimental effects.

The invention also provides methods for treating cancer by increasing an immune response in the subject, comprising administering a compound of formula A to said subject. The invention also provides methods of treating CD4 T cell-linked immunodeficiency associated with cancer in a subject by administering a compound of formula A to said subject.

The duration, dosages and frequency of administering compounds or compositions of the invention may be adapted according to the subject and disease. The treatment may be used alone or in combination with other active ingredients, either simultaneously or separately or sequentially.

The compounds or compositions according to the invention may be administered in various ways or routes such as, without limitation, by systemic injection, intramuscular, intravenous, intraperitoneal, cutaneous, subcutaneous, dermic, transdermic, intrathecal, ocular (for example corneal) or rectal way, or by a topic administration on an inflammation site, and preferably by intramuscular or intravenous injection.

A typical regimen comprises a single or repeated administration of an effective amount of a compound of formula A over a period of one or several days, up to one year, and including between one week and about six months. It is understood that the dosage of a pharmaceutical compound or composition of the invention administered in vivo will be dependent upon the age, health, sex, and weight of the recipient (subject), kind of concurrent treatment, if any, frequency of treatment, and the nature of the pharmaceutical effect desired. The ranges of effectives doses provided herein are not intended to be limiting and represent preferred dose ranges. However, the most preferred dosage will be tailored to the individual subject, as is understood and determinable by one skilled in the relevant arts (see, e.g., Berkowet et al., eds., The Merck Manual, 16$^{th}$ edition, Merck and Co., Rahway, N.J., 1992; Goodmanetna., eds., Goodman and Cilman's The pharmacological Basis of Therapeutics, 10$^{th}$ edition, Pergamon Press, Inc., Elmsford, N.Y., (2001)).

Further aspects and advantages of the invention are disclosed in the following experimental section, which shall be considered as illustrative.

Examples

Patients and Methods

Origin of the Plasma

Viremic patients (VP) included in the study had been HIV-positive for more than one year. They did not receive any antiretroviral drugs and had a viral load >10,000 RNA copies/ml with a CD4 count >200/ml at the time of blood collection (ANRS EP 33 and EP20 studies). All blood samples from VP were drawn at Hôpital Bicêtre or Centre Hospitalier de Gonesse.

Production of Recombinant PLA2GIB Enzyme sPLA2GIB was produced in *E. Coli*. Inclusion bodies were solubilized in urea and afterwards renatured. sPLA2GIB was further purified by HPLC. Homogeneity of the preparations was verified by MassSpectrometry (Maldit-off). The specific activity of the enzyme was always measured and compared to standard preparations.

Bioassays

Inhibition of IL-7-induced phosphorylated STAT5 nuclear translocation (NTpSTAT) was measured as follows: VP plasma (5 or 10%) was first incubated with purified HD CD4 T cells (20 min) before stimulation by IL-7 (2 nM, 15 min.). Cells were then plated on polylysine coated glass slides before fixation by PFA (1.5%) and permeabilization by methanol (90% at −20° C.). pSTAT5 was then stained by rabbit anti-STAT5 and labeled with goat anti-rabbit-Atto642. The cells were analyzed by pulsed STED microscopy and the number of nuclei expressing pSTAT5 were counted.

Compound

Peptide I (cyclic(2-NaphthylAla-Leu-Ser-2-NaphthylAla-Arg)) was obtained from Calbiochem. The compound was solubilized in DMSO before use.

Results

Figure 2:
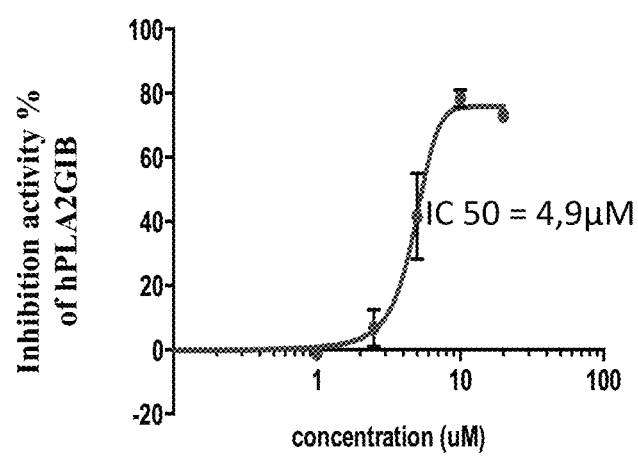
FIG. 2: Calculation of IC50 of Peptide I: Experimental data were analyzed by Prism software in order to precisely calculate the IC50.

We first investigated the effects of different doses of Peptide I on the biological activity of recombinant PLA2GIB as tested in the bioassay described in Materials and Methods. FIG. 1 shows that the inhibitory effect of Peptide I is effective at 5 microM and very strong at 10 microM. The experiment was repeated twice. From the experimental data we derived the corresponding theoretical curve that gives the IC50. For Peptide I, IC 50 is about 4.9 microM (FIG. 2).

We have shown that PLA2 GIB contained in the plasma of viremic patients induces a blockade of IL-7-induced nuclear translocation of phospho STAT5 (NT pSTAT5). Consequently, CD4 T lymphocytes purified from healthy donors and exposed to viremic plasma do not respond to IL-7. Here we tested the effects of Peptide I on the capacity of the sera from VP to block IL-7-induced NTpSTAT5.

Figure 3:
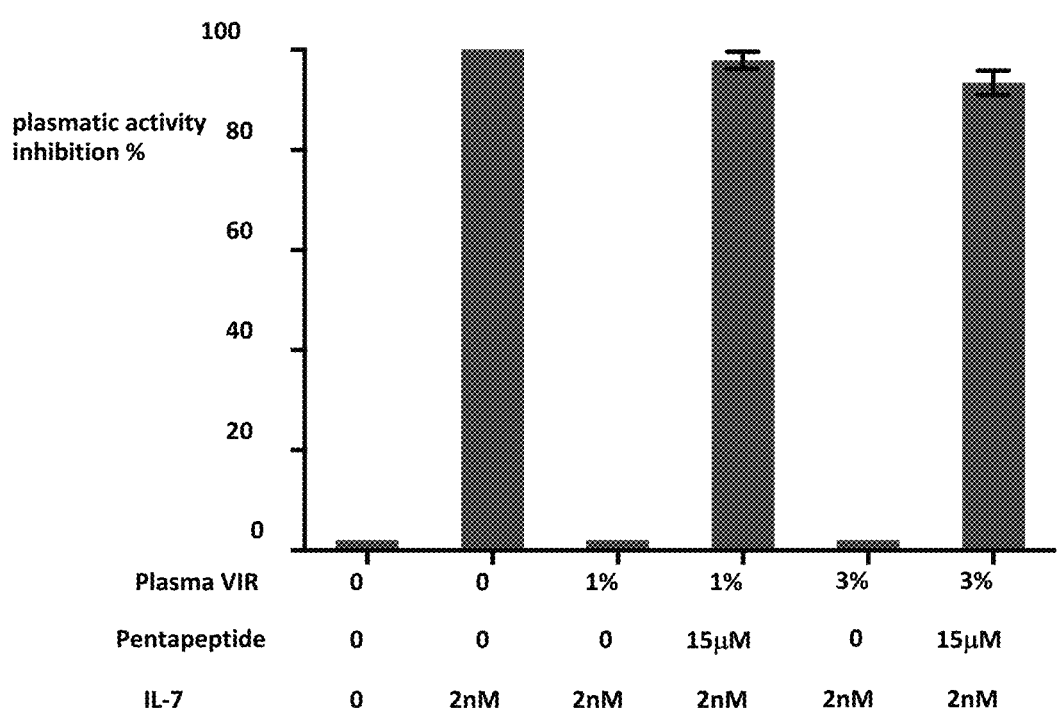
FIG. 3: Peptide I restores the activity of CD4 lymphocytes: CD4 lymphocytes purified from healthy donors were exposed to sera from viremic HIV-infected patients at 1% or 3% dilution. Such exposure resulted in a complete inhibition of IL-7-induced nuclear translocation of pSTAT5. At 15 microM, Peptide I totally reversed this inhibition, thus restoring CD4 function. Five sera were tested and the results are given as the median+/−SD.

The effect of plasma from various HIV viremic patients (at least 5) were titrated on the inhibition of IL-7-induced NTpSTAT5. In the experiments, we first used plasma at 1% dilution, and then at 3% dilution which gives between 30 to 70% of the maximum inhibition. Under these experimental conditions, we show that at 15 microM (3 times the IC50), Peptide I completely reverted the activity of the sera (FIG. 3).

Peptide I is thus able to revert the inhibitory activity of the plasma of viremic patients. It is worth noting that Peptide I is even more active when contained in the plasma of the patients than against the recombinant pure enzyme contained in serum free buffer. The inhibition obtained with the recombinant enzyme reaches a plateau corresponding to a maximum inhibition of around 80%. By contrast, when the plasma is used, inhibition of around 100% is achieved (compare data of FIG. 1 with data FIG. 3). This indicates that Peptide I is highly active in the plasma despite the high concentration of many proteins and the presence of several lipid moieties which could interfere with PLA2GIB and hide the access to the catalytic site after organization on multimolecular complexes of high molecular weight which could therefore impede the effects of Peptide I.

DISCUSSION

We previously demonstrated that PLA2GIB induces at the CD4 T lymphocyte level various defects that characterize CD4 T cells from viremic patients. We reported the inability to respond to IL-7 which explains lymphopenia. We extended this observation and demonstrated the inability of PLA2GIB-treated CD4 lymphocytes to respond to IL-2 or to IL-4, thus explaining anergy.

Here, for the first time, we describe compounds which, through a strong inhibition of the enzymatic activity of PLA2G1B found in the plasma of viremic HIV-infected patients, completely reverted the deleterious effects of PLA2GIB co. Importantly, Peptide I was able to neutralize the pathogenic activity of the sera from all viremic patients tested. The effects observed are total, clearly pointing out to the strong potential of this therapeutic approach.

REFERENCES (1) Grossman Z, Meier-Schellersheim M, Sousa A E, Victorino R M M, Paul W E (2002) CD4+ T-cell depletion in HIV infection: are we closer to understanding the cause? Nat Med 8(4):319-323.
(2) Catalfamo M, et al. (2008) HIV infection-associated immune activation occurs by two distinct pathways that differentially affect CD4 and CD8 T cells. *PNAS* 105(50): 19851-19856.
(3) Armah K A, et al. (2012) HIV status, burden of comorbid disease and biomarkers of inflammation, altered coagulation, and monocyte activation. *Clin Infec Dis* 55(1)126-36.

The invention claimed is:

1. A method of inducing or stimulating an immune response in a subject in need thereof, comprising administering to the subject a peptide comprising the sequence AA1-Leu-AA3-AA4-AA5 or a pharmaceutical composition comprising said peptide, wherein:
- AA1 designates Phe, Leu, norleucine, tryptophan, 2-naphthylalanine (2NapA), or 1-naphthylalanine (1NapA);
- AA3 designates Ser, Thr or Cys;
- AA4 designates Tyr, 2-naphthylalanine (2NapA), 1-naphthylalanine (1NapA), diphenylalanine, 7-hydroxyltetrahydroisoquinoline (7HTiq), or tetrahydroisoquinoline (Tiq); and
- AA5 designates Lys, Arg, or citrulline;
or a salt, hydrate, racemate or enantiomer thereof, and wherein the subject has a CD4 T cell-related immunodeficiency caused by a viral infection.

2. The method of claim 1, wherein:
- AA1 designates Phe or 2NapA;
- AA3 designates Ser;
- AA4 designates Tyr or 2NapA; and
- AA5 designates Lys or Arg;
or a salt, hydrate, racemate or enantiomer thereof.

3. The method of claim 1, wherein the peptide is cyclic.

4. The method of claim 1, wherein the peptide is cyclic (2-NaphthylAla)-Leu-Ser-(2-NaphthylAla)-Arg, or a salt, hydrate, racemate or enantiomer thereof.

5. The method of claim 1, wherein the viral infection is an HIV-infection.

6. The method of claim 1, wherein the peptide is administered to the subject at a dose between 0.01 μg and 100 mg.

7. The method of claim 1, wherein the peptide is administered repeatedly to the subject.

8. The method of claim 1, wherein the peptide is administered by injection, nasally, orally, mucosal, rectally or by inhalation.

9. The method of claim 1, wherein the peptide is formulated in a pharmaceutical composition comprising a pharmaceutically acceptable carrier or excipient.

10. The method of claim 1, wherein the subject is a human subject.

11. The method of claim 1, wherein the peptide inhibits secreted phospholipase A2 group IB (sPLA2GIB) in the subject having the CD4 T cell-related immunodeficiency.

12. A method of treating a subject having a CD4 T cell-related viral disease, comprising administering to the subject in need thereof cyclic (2-NaphthylAla)-Leu-Ser-(2-NaphthylAla)-Arg, or a salt, hydrate, racemate or enantiomer thereof, in an amount effective for inducing or stimulating CD4 T cells.

\* \* \* \* \*

SEQUENCE LISTING

```
<160> NUMBER OF SEQ ID NOS: 14

<210> SEQ ID NO 1
<211> LENGTH: 5
<212> TYPE: PRT
<213> ORGANISM: ARTIFICIAL
<220> FEATURE:
<223> OTHER INFORMATION: peptide

<400> SEQUENCE: 1

Phe Leu Ser Tyr Lys
1               5

<210> SEQ ID NO 2
<211> LENGTH: 5
<212> TYPE: PRT
<213> ORGANISM: ARTIFICIAL
<220> FEATURE:
<223> OTHER INFORMATION: peptide

<400> SEQUENCE: 2

Phe Leu Ser Tyr Arg
1               5

<210> SEQ ID NO 3
<211> LENGTH: 5
<212> TYPE: PRT
<213> ORGANISM: ARTIFICIAL
<220> FEATURE:
<223> OTHER INFORMATION: peptide
<220> FEATURE:
<221> NAME/KEY: MISC_FEATURE
```

```
<222> LOCATION: (1)..(1)
<223> OTHER INFORMATION: X is 2-NaphtylAlanine
<220> FEATURE:
<221> NAME/KEY: MISC_FEATURE
<222> LOCATION: (4)..(4)
<223> OTHER INFORMATION: X is 2-NaphtylAlanine

<400> SEQUENCE: 3

Xaa Leu Ser Xaa Arg
1               5

<210> SEQ ID NO 4
<211> LENGTH: 5
<212> TYPE: PRT
<213> ORGANISM: ARTIFICIAL
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: X is 2-NaphtylAlanine

<400> SEQUENCE: 4

Xaa Leu Ser Tyr Arg
1               5

<210> SEQ ID NO 5
<211> LENGTH: 5
<212> TYPE: PRT
<213> ORGANISM: ARTIFICIAL
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: X is 2-NaphtylAlanine

<400> SEQUENCE: 5

Phe Leu Ser Xaa Arg
1               5

<210> SEQ ID NO 6
<211> LENGTH: 5
<212> TYPE: PRT
<213> ORGANISM: ARTIFICIAL
<220> FEATURE:
<223> OTHER INFORMATION: peptide

<400> SEQUENCE: 6

Gly Cys Gly Ser Tyr
1               5

<210> SEQ ID NO 7
<211> LENGTH: 5
<212> TYPE: PRT
<213> ORGANISM: ARTIFICIAL
<220> FEATURE:
<223> OTHER INFORMATION: peptide

<400> SEQUENCE: 7

Gly Cys Gly Ser Pro
1               5

<210> SEQ ID NO 8
<211> LENGTH: 5
<212> TYPE: PRT
<213> ORGANISM: ARTIFICIAL
<220> FEATURE:
<223> OTHER INFORMATION: peptide
```

```
<400> SEQUENCE: 8

Thr His Thr Tyr Ser
1               5

<210> SEQ ID NO 9
<211> LENGTH: 5
<212> TYPE: PRT
<213> ORGANISM: ARTIFICIAL
<220> FEATURE:
<223> OTHER INFORMATION: peptide

<400> SEQUENCE: 9

Lys Asp Tyr Tyr Arg
1               5

<210> SEQ ID NO 10
<211> LENGTH: 5
<212> TYPE: PRT
<213> ORGANISM: ARTIFICIAL
<220> FEATURE:
<223> OTHER INFORMATION: peptide

<400> SEQUENCE: 10

Leu Glu Lys Tyr Leu
1               5

<210> SEQ ID NO 11
<211> LENGTH: 5
<212> TYPE: PRT
<213> ORGANISM: ARTIFICIAL
<220> FEATURE:
<223> OTHER INFORMATION: peptide

<400> SEQUENCE: 11

Val Asp His Tyr Asp
1               5

<210> SEQ ID NO 12
<211> LENGTH: 5
<212> TYPE: PRT
<213> ORGANISM: ARTIFICIAL
<220> FEATURE:
<223> OTHER INFORMATION: peptide

<400> SEQUENCE: 12

Thr Gln Ser Tyr Lys
1               5

<210> SEQ ID NO 13
<211> LENGTH: 5
<212> TYPE: PRT
<213> ORGANISM: ARTIFICIAL
<220> FEATURE:
<223> OTHER INFORMATION: peptide

<400> SEQUENCE: 13

Thr Glu Arg Tyr Ser
1               5

<210> SEQ ID NO 14
<211> LENGTH: 5
<212> TYPE: PRT
<213> ORGANISM: ARTIFICIAL
<220> FEATURE:
<223> OTHER INFORMATION: peptide
```

```
<400> SEQUENCE: 14

His Glu Thr Ala Trp
1               5
```